United States Patent
Kulkarni et al.

(10) Patent No.: US 12,213,798 B2
(45) Date of Patent: Feb. 4, 2025

(54) ADHERENCE-TRACKING AND MONITORING DEVICE FOR METERED-DOSE INHALER

(71) Applicant: CIPLA LIMITED, Maharashtra (IN)

(72) Inventors: Nandan Kulkarni, Maharashtra (IN); Geena Malhotra, Maharashtra (IN); Brinder Ahluwalia, Karnataka (IN); Mohnish Jagdish Zaveri, Maharashtra (IN)

(73) Assignee: CIPLA LIMITED, Mumbai (IN)

( * ) Notice: Subject to any disclaimer, the term of this patent is extended or adjusted under 35 U.S.C. 154(b) by 462 days.

(21) Appl. No.: 16/630,391

(22) PCT Filed: Jul. 11, 2018

(86) PCT No.: PCT/IN2018/050454
§ 371 (c)(1),
(2) Date: Jan. 10, 2020

(87) PCT Pub. No.: WO2019/012558
PCT Pub. Date: Jan. 17, 2019

(65) Prior Publication Data
US 2021/0059600 A1 Mar. 4, 2021

(30) Foreign Application Priority Data
Jul. 11, 2017 (IN) .............................. 201721024423

(51) Int. Cl.
*A61M 15/00* (2006.01)
*A61B 5/00* (2006.01)
(Continued)

(52) U.S. Cl.
CPC ............ *A61B 5/4833* (2013.01); *A61B 5/746* (2013.01); *A61M 15/0026* (2014.02);
(Continued)

(58) Field of Classification Search
CPC ............ A61M 15/0026; A61M 15/008; A61M 15/009; A61B 5/4833; A61B 5/746
See application file for complete search history.

(56) References Cited

U.S. PATENT DOCUMENTS 5,284,133 A 2/1994 Burns et al.
5,363,842 A 11/1994 Mishelevich et al.
(Continued)

FOREIGN PATENT DOCUMENTS

CN 105163784 A 12/2015
JP 2016-514511 A 5/2016
(Continued)

OTHER PUBLICATIONS

International Search Report mailed Dec. 27, 2018 in International Patent Application No. PCT/IN2018/050454.
(Continued)

*Primary Examiner* — Timothy A Stanis
(74) *Attorney, Agent, or Firm* — Knobbe, Martens, Olson & Bear, LLP

(57) ABSTRACT

An adherence-monitoring and tracking device captures usage of a metered dose inhaler (MDI). The device includes an enclosure for enclosing a metered dose inhaler (MDI), and an electro-mechanical system forming a part of enclosure to sense and log the operation of the MDI. The electro-mechanical system includes at-least one transducer to capture one or more parameters pertaining to an operation of the MDI by the user. A microcontroller processes the captured parameters, and an output-unit renders data pertaining to operation of the MDI.

16 Claims, 9 Drawing Sheets

(51) Int. Cl.
  *G16H 20/10* (2018.01)
  *G16H 20/13* (2018.01)
  *G16H 40/67* (2018.01)

(52) U.S. Cl.
  CPC ........ *A61M 15/008* (2014.02); *A61M 15/009* (2013.01); *G16H 20/13* (2018.01); *G16H 40/67* (2018.01); *A61M 2205/18* (2013.01); *A61M 2205/3331* (2013.01); *A61M 2205/3334* (2013.01); *A61M 2205/3375* (2013.01); *A61M 2205/52* (2013.01); *A61M 2205/583* (2013.01); *A61M 2205/587* (2013.01); *A61M 2205/8206* (2013.01)

(56) References Cited

U.S. PATENT DOCUMENTS

| | | |
|---|---|---|
| 6,958,691 B1 | 10/2005 | Anderson et al. |
| 8,474,448 B2 | 7/2013 | Oi et al. |
| 8,567,394 B2 | 10/2013 | Herder et al. |
| 8,807,131 B1 | 8/2014 | Tunnell et al. |
| D787,810 S | 5/2017 | Wang et al. |
| 2009/0030285 A1* | 1/2009 | Andersen .................. A61B 7/04 128/200.14 |
| 2009/0194104 A1 | 8/2009 | Van Sickle |
| 2011/0253139 A1* | 10/2011 | Guthrie ............. A61M 15/0005 128/203.14 |
| 2014/0182584 A1 | 7/2014 | Sutherland et al. |
| 2015/0100335 A1* | 4/2015 | Englehard ......... A61M 15/0093 705/2 |
| 2015/0112707 A1 | 4/2015 | Manice et al. |
| 2015/0249478 A1* | 9/2015 | Greiner ..................... A61J 1/03 455/575.8 |
| 2016/0022933 A1 | 1/2016 | Ciancone et al. |
| 2016/0051776 A1 | 2/2016 | Von Hollen |
| 2016/0144141 A1 | 5/2016 | Biswas et al. |
| 2016/0228657 A1 | 8/2016 | Sutherland |
| 2016/0325058 A1* | 11/2016 | Samson ............... A61B 5/0022 |
| 2017/0290527 A1* | 10/2017 | Morrison ............... A61B 5/097 |
| 2017/0325734 A1* | 11/2017 | Sutherland ........ A61M 15/0041 |
| 2020/0086069 A1* | 3/2020 | Riebe .................. A61M 15/009 |
| 2020/0405579 A1* | 12/2020 | Shukla .................... G16H 40/63 |

FOREIGN PATENT DOCUMENTS

| | | | |
|---|---|---|---|
| WO | WO 2014/004437 A1 | 1/2014 |
| WO | WO 2016/111633 A1 | 7/2016 |
| WO | WO 2017/051389 A1 | 3/2017 |
| WO | WO 2019/012558 A1 | 1/2019 |

OTHER PUBLICATIONS

Written Opinion of the International Searching Authority mailed Dec. 27, 2018 in International Patent Application No. PCT/IN2018/050454.

* cited by examiner

ADHERENCE-TRACKING AND MONITORING DEVICE FOR METERED-DOSE INHALER

FIELD OF THE INVENTION

The present disclosure relates to metered dose inhalers (MDI) and in particular relates to a device that captures operation of the MDI.

BACKGROUND AND PRIOR ART

Typically known devices for delivering aerosol medications for inhalation by patient include metered dose inhaler that are manually operated and breath-actuated. The metering dose inhaler body contains a receptacle for the canister, a valve assembly and an actuator. The actuator contains a flow path which terminates a nozzle and receives a valve stem in alignment with the flow path. The valve-stem is typically passive and hence when the canister is pressed relative to the valve stem receptacle, by manual or automatic advance, the valve stem is pressed into the metering valve and releases the dose through the flow path and out of the nozzle.

The effectiveness of any inhaler is based upon compliance with the treatment regime and accordingly poses a challenge when adherence becomes difficult to manage and measure. Millions of patients in the United States who suffer from chronic asthma exhibit a poor adherence rate that greatly contributes to billions of annual medical expenditure (indirect and direct). On an average, children and adult adhere to their prescribed medication schedule with less than 50% success rate (i.e. they skip their medication more than 50% of time). Additionally, a poor technique (i.e. missing one or more critical step in the pMDI inhalation maneuver) coupled with a poor coordination (between the actuation of the dose and inhalation of the same in correct manner) leads to ineffectiveness of the undertaken dose, and may sometimes be equivalent to null dosage.

As a solution, there exists adherence tracking-devices that are typically used in conjecture with the conventional pMDI either as an integrated part of it or as additional accessory. These devices have been known in the academic and clinical research settings and use a combination of pneumotachometer class sensors, audio sensors and or recording systems to monitor the usage of pMDI devices and record this data without patient intervention. One such example is Smart-Touch™ by AstraZeneca to be used in combination with Symbicort® actuator. Other example is the research work done by Prof. Richard Costello and his group using INCA (The Inhaler Compliance Assessment) system used in combination with Advair Diskus.

Examples of recently developed electronic adherence-tracking devices include a compliance tracking system that CoheroHealth® developed as a connected health device to help children with asthma, particularly their parents, to manage medication adherence. It deploys a system of jacket-type electronic device or integrated electronic housing with the pMDI actuator, a mobile application to read the data from the device and records adherence to the dose regimen for the patient along with provision for reminders to take dose. Other example of such tracking device is powered by an application provided by United States based digital health solution provider "Propeller Health". Said application works in tandem with technology-company Propeller Health's respiratory monitoring sensor—a mountable digital device that can be attached to an inhaler to record usage data. The recorded data is communicated to a user's phone via an application, offering insights into an individual's asthma triggers.

Another problem that has lingered for a long-time is patient visiting the physician and having an extremely imperfect recollection as to how frequently the inhaler has been used. As a solution, interactive respiratory device usage tracking system has been in existence for some time. Solutions proposed to this problem in the literature include those described in U.S. Pat. Nos. 6,958,691, 5,363,842, US patent application 2011/0253139, US patent application 2009/0194104 and published international application WO 2014/004437.

US patent application 2015/0112707 describes inhaler use monitoring system that includes a tracker module adaptable to be secured to a variety of inhalers and having an activation sensor for sensing the use of inhaler, an internal memory for storing inhaler data and a communications component for forwarding the stored data to a processor for analyzing the data.

U.S. Pat. No. 5,284,133 describes a dose timer, actuator mechanism and patient compliance monitoring means. The invention relates to a dose or timing controlled actuator that operates in conjunction with an inhalation device to prevent both patient under-compliance with prescribed medication and patient abuse of or dependence on prescribed medication.

Yet, a major drawback across all of the prior arts is that the solutions are often bulky, require a customized inhaler (i.e. adherence-monitoring devices cannot be easily fitted to and operated with conventionally existing inhalers), require a specific hardware to act as a data-logger, collect data and forward it to the physician.

Another problem associated with the known solutions is that all of the existing adherence-monitoring solutions have inadequate provision to encourage and incentivize adherence and lack ability to accurately record the technique and establish coordination between the inhalation and exhalation maneuver for pMDI usage.

Yet, another major problem with conventional adherence-monitoring devices is that a large battery size or frequent replacement of batteries is needed owing to enormous power-consumption by the processor, transmitter and sensors, thereby limiting the life of the device on a stand-alone basis.

Yet, another problem with existing tracking and adherence monitoring devices is inability to receive a real-time feedback in respect of the data-generated during a patient-usage of the inhaler to actively control the actuation based on patient breathing profile.

SUMMARY OF THE INVENTION

This summary is provided to introduce a selection of concepts in a simplified format that are further described in the detailed description of the invention. This summary is not intended to identify key or essential inventive concepts of the invention, nor is it intended for determining the scope of the invention.

In an embodiment, the present subject matter describes an adherence-monitoring and tracking device for capturing usage of a metered dose inhaler (MDI). The device comprises an enclosure for enclosing a metered dose inhaler (MDI), and an electro-mechanical system forming a part of enclosure to sense and log the operation of the MDI. The electro-mechanical system comprises at-least one transducer to capture one or more parameters pertaining to an operation of the MDI by the user; a microcontroller to process said captured parameters, and an output-unit for rendering data pertaining to operation of the MDI.

In another embodiment, the adherence-monitoring and tracking device comprises an enclosure for accommodating a metered dose inhaler (MDI). The enclosure comprises a hollow cylindrical-portion for receiving the MDI, a foldable-flap integral to the cylindrical portion from a first end for covering the top portion of the MDI, a plurality of magnetic-contacts to latch the second end of the flap to the cylindrical portion, and an electro-mechanical system forming a part of enclosure to capture the operation of the MDI and electronically render data thereof.

In another embodiment, the adherence-monitoring and tracking device comprises a housing for accommodating a metered dose inhaler (MDI) defined by an assembly of a canister and a mouth-piece. The housing comprises an elongated hollow-block open at the bottom for accommodating a canister of the MDI; and a cover hinged at the bottom of the hollow-block. The hinged-cover is rotatable to act as a removable-lid at the bottom of the hollow-block and thereby selectively cover a mouthpiece linked to the canister accommodated in the hollow-block. An electro-mechanical system is supported within the housing to capture the operation of the MDI and electronically-render data associated thereto.

In an implementation, the microcontroller within the device is adapted to process data received from one or more sensors to provide information pertaining to at least one of:
a) dose left in the device,
b) a schedule of the next dose based on a pre-stored prescription; and
c) adherence to the dosage regime as a percentage and absolute number based on an elapse of time as well as drug prescribed In an embodiment, the microcontroller processes the data received from said one or more sensors to execute one or more of:
real-time tracking of the inhalation flow rate;
deriving an inhalation-profile of the user;
identifying a triggering flow-rate by self-calibrating the inhalation profile In an implementation, the microcontroller upon having received data from said one more sensors located within the device is adapted to determine correctness or error of operation due to execution of one or more of:
a) number of steps in the inhalation maneuver
b) shaking of the MDI before use,
c) opening of the actuator cap,
d) exhalation before inhalation,
e) inhalation for a certain duration before and after spray is actuated; and
f) closure of the cap; and
g) preparation for the second dose,
wherein said error of operation is triggered upon having referred said created inhalation-profile.

In an implementation, the microcontroller upon having received data from said one or more sensors located within the device is adapted to ascertain correctness in the technique of coordination between the inhalation and actuation based on one or more of:
a) orientation of the MDI;
b) timing of the actuation;
c) inhalation flow-rate profile received from the device.

In an implementation, the microcontroller based on aforesaid processing causes:

generation of consolidated data at-least based on dose-schedule, adherence, pre-stored medical-prescriptions for a patient; and
synchronizes the generated data periodically with an external-storage.
record the parameters involved in an inhalation-maneuver schedule of the next dose based on a pre-stored prescription;
depiction of adherence to the dosage-regime as a percentage and/or absolute number as a function of time and/or drug prescribed.

In an implementation, the microcontroller based on aforesaid processing causes a display of one or more of:
dosages undertaken by the user;
validity of steps within the pMDI inhalation maneuver;
validity of coordination between actuation and inhalation maneuver;
alerts in respect of errors made during the preparation, usage or post usage of the pMDI device At least based on aforesaid embodiments, the present subject matter provides an electronic reusable jacket and an application (e.g. a smartphone based app) linked with it for tracking, adherence, monitoring and coordination-control during the usage of conventionally available pMDI devices, while not requiring any modification required in the existing actuators or drug containing canisters.

Conventional electronic tracking-devices are integrated into the actuator-body of the pMDI and merely provide posterior-information regarding the operation of the metered dose inhaler. Examples of such posterior information may be timing of the dose taken, and correctness of steps in preparation and usage of the pMDI. In sharp contrast, the present subject matter captures real-time data during the actuation, processes it for actively providing feedback to a patient during and after inhalation-maneuvers, and guides the patient to improve coordination and technique in the usage of pMDI. Also, the present subject matter provides this feedback that is customized with respect to the inhalation profile of the patient, based on inhalation flow rate and pattern of usage of pMDI.

The device also renders on-board electronic display that provides user details about each of the actuation including the dose taken, correctness of steps in pMDI inhalation maneuver, correctness of coordination and flash any crucial errors made during the preparation, usage or post usage of the pMDI device, thereby enabling the device to function as a standalone device in case of unavailability of mobile phone application.

Further, as a part of rendering the outcome, the application linked to the present adherence-monitoring and tracking device may be implemented on a mobile or tablet (e.g. Android and iOS platform) which uniquely identifies the device of the patient, connects and pairs with it automatically and receives the data transmitted by the device As per the present subject-matter, the real-time data gathered during the actuation is processed to actively control a trigger-timing during the inhalation maneuvers as well as control the time of inhalation to maximize coordination between actuation and inhalation. Further, the triggering is customized in accordance with the profile of the user during each dose taken.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1:
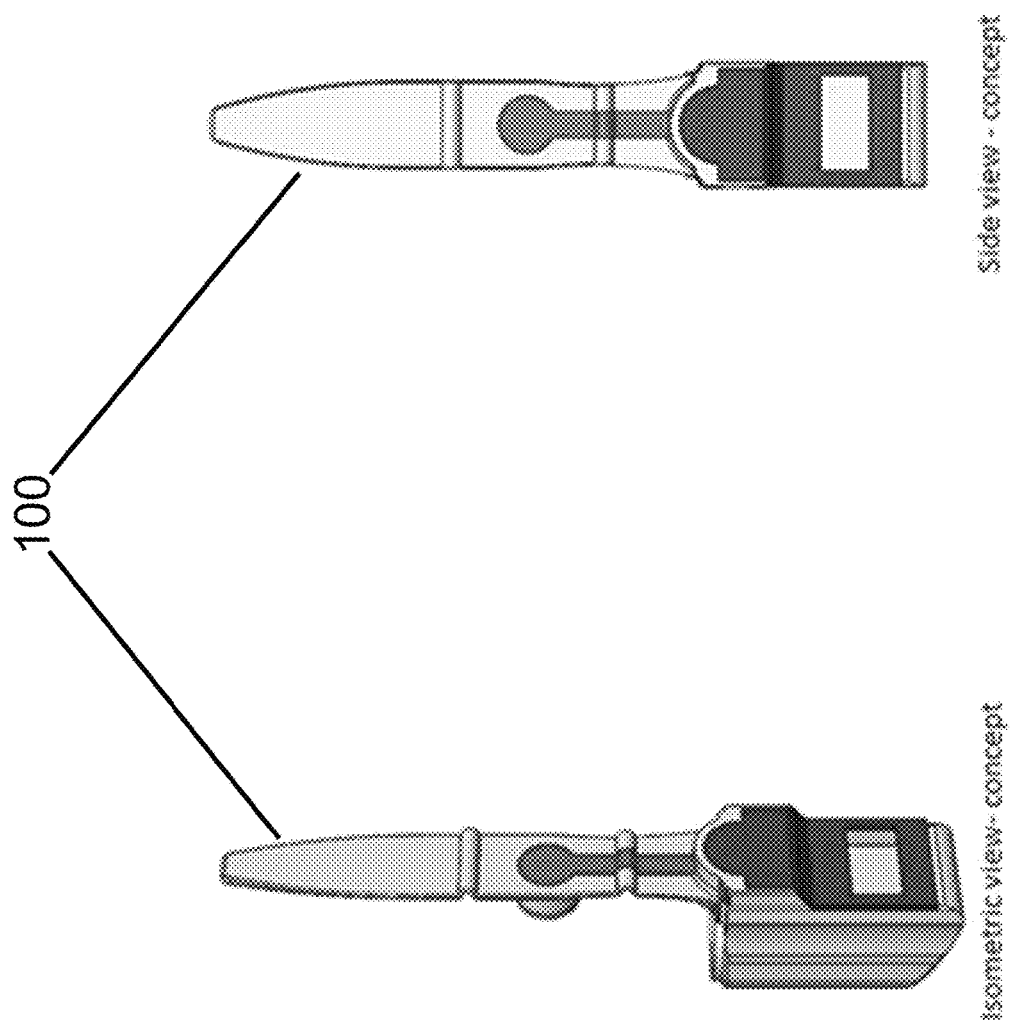
FIG. 1 illustrates schematic views of the adherence-tracking and monitoring-device, in accordance with an embodiment of the present invention.

The elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION OF FIGURES

For the purpose of promoting an understanding of the principles of the present disclosure, reference will now be made to the embodiment illustrated in the drawings and specific language will be used to describe the same. It will nevertheless be understood that no limitation of the scope of the present disclosure is thereby intended, such alterations and further modifications in the illustrated system, and such further applications of the principles of the present disclosure as illustrated therein being contemplated as would normally occur to one skilled in the art to which the present disclosure relates.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this present disclosure belongs. The system, methods, and examples provided herein are illustrative only and not intended to be limiting.

Embodiments of the present disclosure will be described below in detail with reference to the accompanying drawings.

FIG. 1 (a and b) illustrates isometric and side-views with respect to an adherence monitoring and tracking-device 100 in accordance with an embodiment of the present subject matter. The device 100 comprises an in-built transducer in the form of a pressure-sensor (depicted later in FIG. 3). The device 100 comprises an enclosure to receive a metered-dose inhaler (MDI), it automatically detects inhalation-flow corresponding to the MDI, as the pressure sensor of the device 100 gets oriented in the flow path from a canister to mouthpiece of the MDI. Thereafter, the device 100 feeds data to an in-built microprocessor on a real-time basis at a periodic-interval of at-least 10-milliseconds.

Further, the device 100 may also include another pressure-sensor (not shown in present figures) to facilitate a lip-sensing arrangement (i.e. a lip-pressure measurement). The pressure-transducer is fitted to check the vacuum flow-rate and provide a feedback to the on-board microprocessor, if the medicament was actually inhaled by the patient, and confirm the dose taken. In an example, the transducer in the device 100 may further include a microphone as an acoustic sensor assisting aforesaid operation.

Further, a tracking, adherence monitoring and coordination control module of the present device 100 comprises another transducer as an accelerometer, real-time clock for time-keeping, flash memory for local data storage and a switch of resistance not less than 38 N to actuate the device. In an example, details of constituent electronic components within the control module are given in the exhibit below.

| Component names of control module | Technical description |
|---|---|
| BAL-NRF02D3 | 50 ohm nominal input/conjugate match balun to nRF51822-CEAA and nRF51422-CEAA |
| RESC0402_N | Generic chip capacitor |
| 0402 | Ceramic Capacitors |
| SO16W | Real Time Clock |
| RESC0402_N | Generic chip resistor |
| QFN40P600X600X90-48_N | Nordic microcontroller (RF) nRF51x22 |
| 2450AT18B100 | Antennae |

-continued

| Component names of control module | Technical description |
|---|---|
| SOIC127P794X203-8N | 32K I2C Serial EEPROM |
| PSON125P300X500X120-8N | Pressure Sensor, 20-110 kpa, Lga-8 |
| SOT223-R | LM1117 Voltage Regulator |
| UG-2864HSWEG01 OLED display | OLED Display |
| LGA16-3MM 2.5X2MM | 3-axis 6/12/24 g SPI/I2C accelerometer |
| 32.768KHZ-FC-135 | Crystal 16.00 MHz 8 pF SMD |
|  | Crystal 32.768 KHz SMD |
| 53047-06 | CONNECTOR |
| 53048-02 | CONNECTOR |
| 53048-02 | CONNECTOR |

According to an embodiment, the aforesaid electronics within the control module enables the device 100 to record each dose taken, count the left dose, and store and process this information locally on the device memory. Additionally, it enables the device 100 to record the parameters involved in the inhalation-maneuver including, but not limited to, shaking before use, opening of cap, exhale before inhale, inhale for a certain duration before and after actuation. The processor processes these parameters at periodic sampling interval of not more than 10 milliseconds to give correctness for each step in the actuation maneuver. Additionally, parameters involved in technique monitoring such as orientation, actuation time, inhalation flow rate profile are measured and processed to compute correctness of technique.

The device 100 renders on-board electronic display (shown later in figures) that provides user-details about each of the actuation including the dose taken, correctness of steps in pMDI inhalation maneuver, correctness of coordination and flash any crucial errors made during the preparation, usage or post usage of the pMDI device. The display may also be provided with a toggle menu that can be intuitively used by the patient to look at the details of not only the last dose taken, but also a set of historical undertaken dosages.

The data pertaining to the dosages and details of each actuation are stored locally at on-board memory, thereby enabling the device 100 to be operable as a standalone-device in case of unavailability of a mobile phone application. Further, the device 100 can occasionally sync either with cloud or a mobile device such as a smartphone, thereby thwarting any possibility of losing the data and maintaining confidentiality of the user's personal data.

As a part of wireless-communication systems, the device 100 deploys 'Bluetooth' energy based data transfer mechanism for transmitting recorded data from each actuation to the application developed which works at the smartphone.

As a part of value-additions, the device's captured output and other parameters may be rendered through an application that can be hosted on mobile or tablet (both Android and iOS platform). The application implemented within the smartphone uniquely identifies the present device, connects/pairs with it automatically, and receives data transmitted by the device. The application processes the received-data, continuously tracks the doses taken, time of the dosage parameters within the inhalation-maneuver that the device has recorded, and provides multiple reports to the patient in an interactive way through the user interface. The reports are also customised with respect to each patient based on the profile-information received such as age, gender etc.

Further, the application also allows the registration of multiple profiles at a single platform, thereby eliminating the possibility of inconvenience to patients such as asthmatic children, multiple family members with asthma etc.

Figure 2:
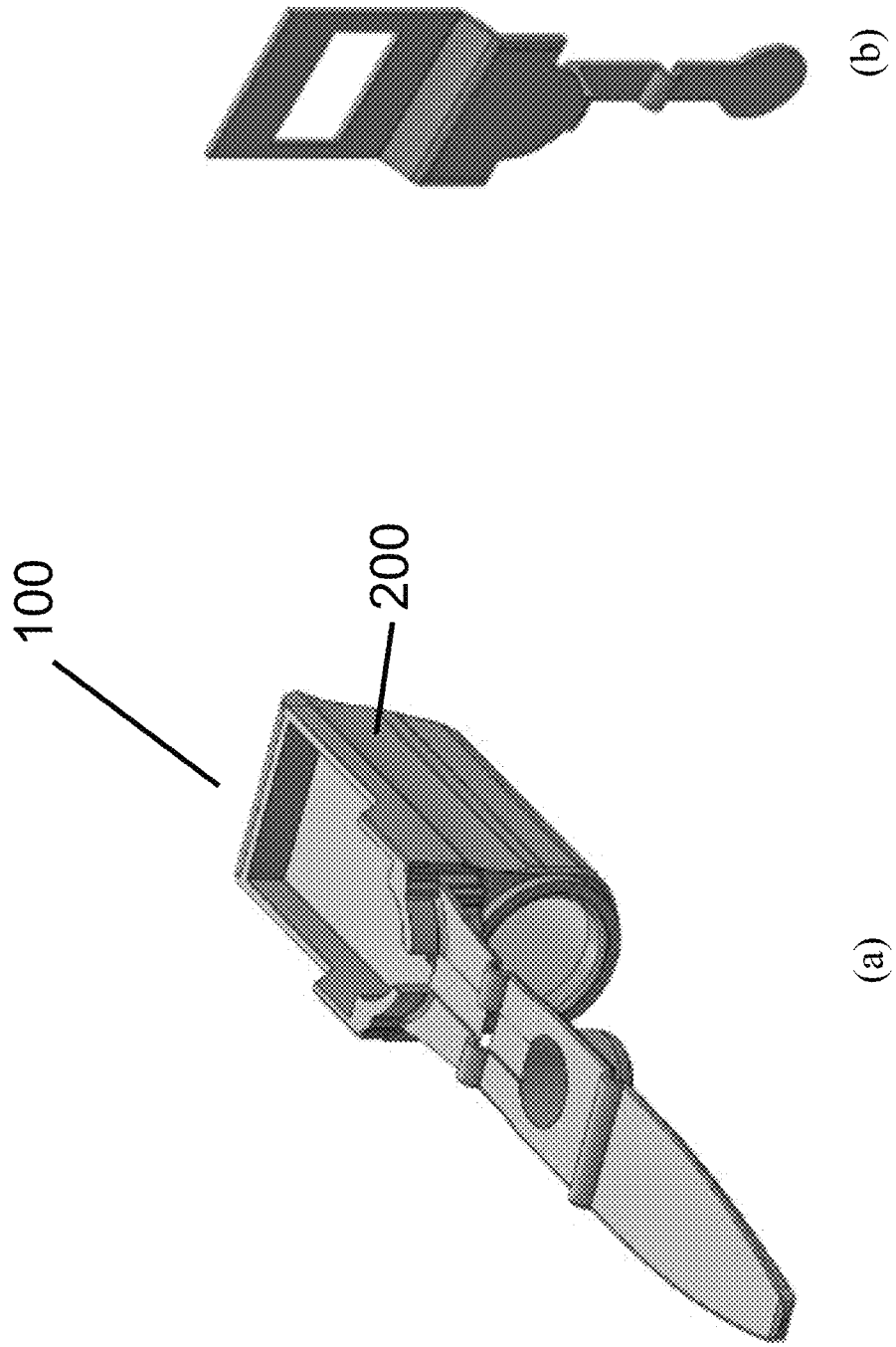
FIG. 2 (a) and (b) illustrate exploded views of the device of FIG. 1, in accordance with an embodiment of the present invention.

FIG. 2 (a and b) illustrates an exploded view of the device 100 of FIG. 1, wherein FIG. 2a represents the structural-component or 'jacket' of the device that includes a hollow enclosure 200 for receiving the MDI. The transducers (i.e. pressure sensor and acoustic sensor) may form a part of enclosure of FIG. 2a. FIG. 2b represents the electronic module which is also shaped to be fitted to the jacket of FIG. 2a. As may be understood from FIG. 2b, the electronic module comprises electronics (microcontroller, memory, register, MEMS such as an accelerometer etc) to process data, and a display module to render the results. Accordingly, the components depicted in FIGS. 2a and 2b are removably connectable with respect to each other and together constitute an electromechanical system.

Figure 3:
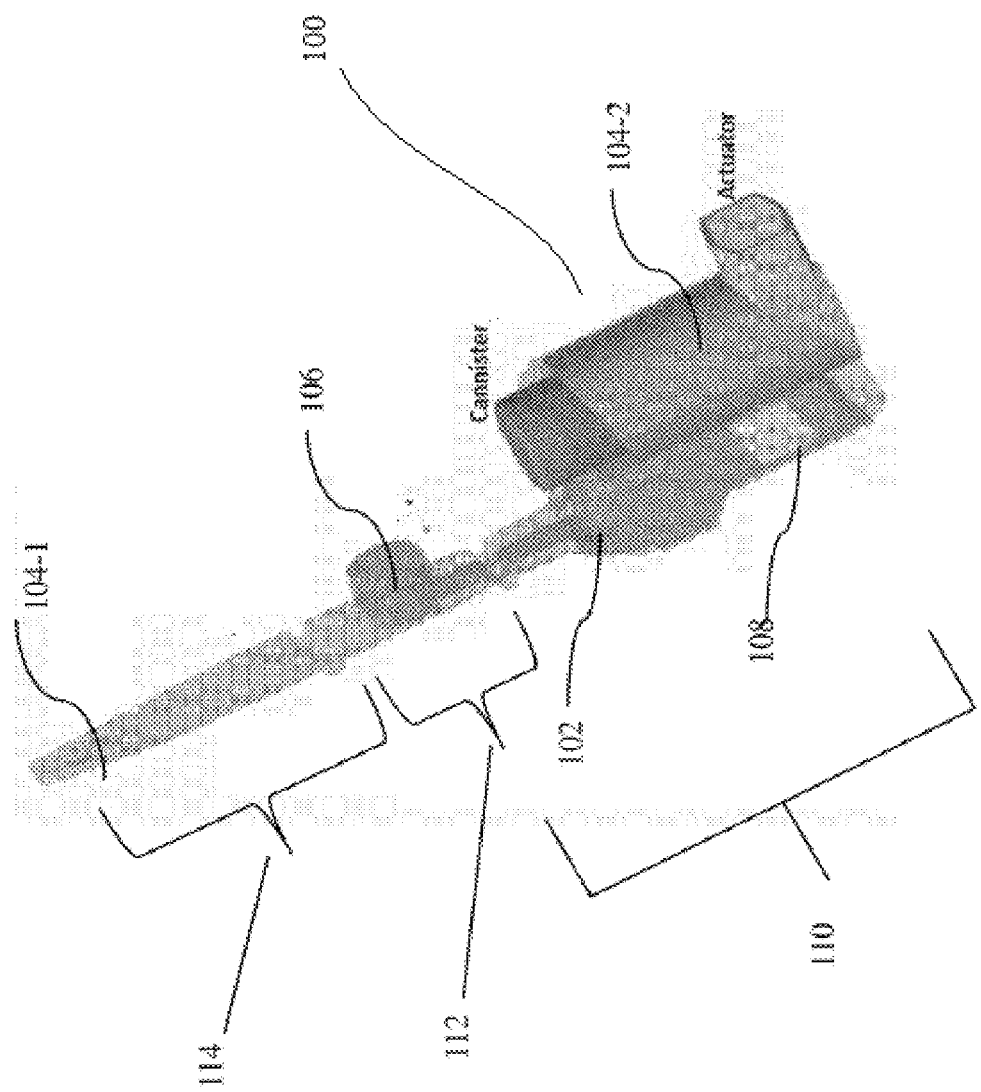
FIG. 3 illustrates an isometric-view of the assembly of the device of FIG. 1 with a conventionally-existing metered dose inhaler, in accordance with an embodiment of the present invention.

FIG. 3 represents an assembly of the device 100 (as depicted in FIG. 1) receiving the MDI (i.e. canister and the actuator) and identifies the components as present within the device 100 and the MDI. In an example, the components as present within the device may be pressure-sensor 102, magnetic-contact points 104-1, 2, microcontroller (not shown in figure), a spring-loaded switch 106, and a display-unit 108. On the other hand, the components of the MDI may be canister and actuator.

In order to encapsulate the device over the metered dose inhaler, the device 100 encloses the MDI through a longitudinal-cover 110, an overhead flap 112, and a longitudinal-flap 114. More specifically, the longitudinal cover 110 comprises the electronics (microcontroller and memory), and is also formed as a hollow-enclosure for receiving the metered dose inhaler. The bendable portions of the device include the overhead flap 112 and the longitudinal flap 114. Accordingly, upon having been bent, while the overhead flap 112 covers the top of canister, the longitudinal flap 114 covers the canister and the actuator body longitudinally like the longitudinal cover, but from a side opposite to the longitudinal cover.

Further, the longitudinal flap 114 comprises a magnetic contact-point 104-1 to ensure that the longitudinal-flap 114 tightly and smoothly latches onto the actuator-body and contacts another magnetic-contact point 104-2 present outside the enclosure receiving the MDI. More specifically, the magnetic point 104-1 contacts the other point 104-2 like a 'tactile-contact' switch, thereby allowing an ease of opening and closure of the longitudinal flap 114.

As far as the overhead flap 112 covering the canister from the top is concerned, a spring-loaded electronic-switch 106 is provided such that the switch 106 and the canister define a substantially-small clearance between them, when the longitudinal-flap is closed using points 104-1, 2 and the overhead flap 112 snugly covers the canister from the top. The spring-loaded switch 106, upon being pressed manually by the user, ensures application of adequate-force (preferably not less than 37 N and not more than 60N) vertically downwards to depress the canister further. Since the switch 106 is electronically connected to the microcontroller, the number of times the switch is actuated facilitates a counting of the correct dose-counting through the electronic module.

Figure 4:
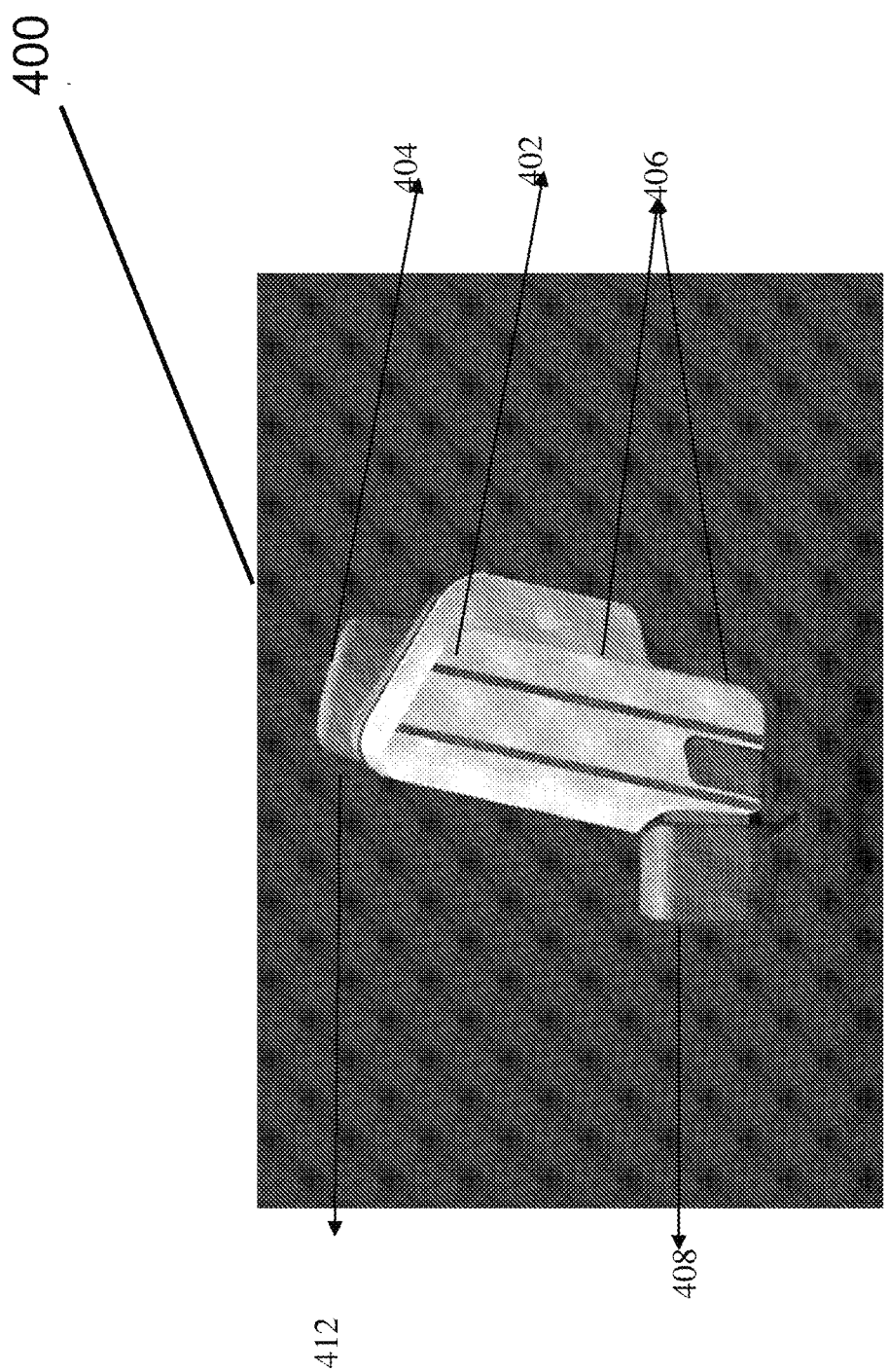
FIG. 4 illustrates a schematic view of an adherence-tracking and monitoring-device, in accordance with another embodiment of the present invention.
Figure 6:
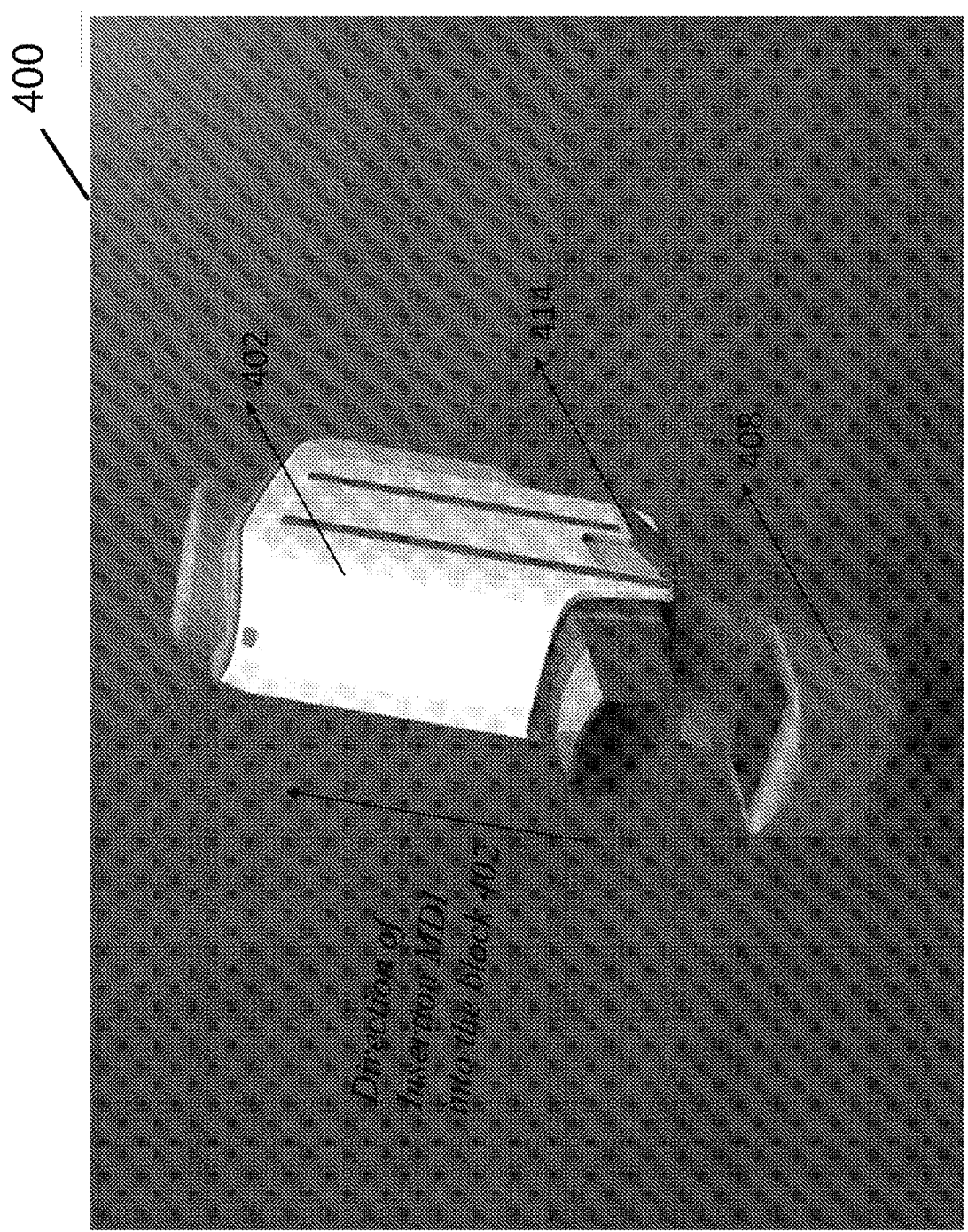
FIG. 6 illustrates the isometric-view of device from the opposite direction as compared to FIG. 5, in accordance with another embodiment of the present invention

FIG. 4 illustrates a schematic view of an adherence-tracking and monitoring-device 400, in accordance with another embodiment of the present invention. The device 400 comprises a housing for accommodating the metered dose inhaler (MDI) and comprises an elongated hollow-block 402 open at the bottom for accommodating a canister of the MDI (in a direction as depicted in FIG. 6). The top of the hollow-block 402 is configured to act as a guide 404 (i.e.

a spring loaded switch) for allowing a user to impose downward-push to the canister for operating the MDI. More specifically, the top of block 402 corresponds to an integrated cap 404 which holds the switch and receives the canister top Further, the hollow block 402 comprises a set of internal ribs to rigidly accommodate the MDI, and a set of external ribs 406 to allow a grip from outside. The internal ribs or internal pinching ribs tightly hold the MDI inside the block 402.

Further, a cover 408 is hinged at the bottom of the hollow-block 402, wherein said hinged cover 408 is rotatable to act as a removable-lid at the bottom of the hollow-block 402 and thereby selectively cover a mouthpiece linked to the canister accommodated in the hollow-block 402. The cover 408 acts as an integrated flexible cap to cover actuator-mouthpiece of the MDI when not in use.

Figure 5:
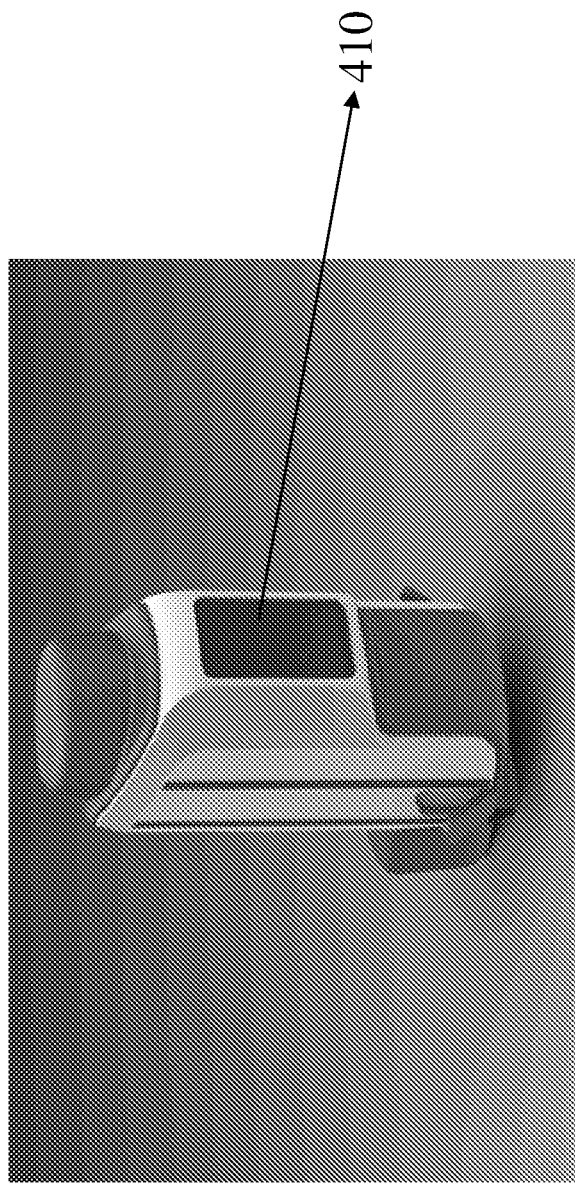
FIG. 5 illustrates an isometric-view of the device of FIG. 4, in accordance with another embodiment of the present invention.

FIG. 5 illustrates an isometric-view of the device 400 of FIG. 4, in accordance with another embodiment of the present invention.

An electro-mechanical system is supported within the housing to capture the operation of the MDI and electronically-render data associated thereto. As a part of said electromechanical system, a display 410 is rendered at the external surface of the hollow-block 402 to electronically render data and alerts. One or more illuminating means 412 (shown in FIG. 6) are connected to the electromechanical-system and supported at the external surface of the hollow-block 402 to provide visible-alerts in real-time.

FIG. 6 illustrates the isometric-view of device 400 from the opposite direction as compared to FIG. 5, in accordance with another embodiment of the present invention. As shown, a locking arrangement 414 is provided to latch the cover 408 with the hollow-block 402 to thereby cause a rigid-accommodation of the mouthpiece within the cover 408 during non-usage of the MDI. Such locking arrangement 414 corresponds to flexible flaps.

Figure 7:
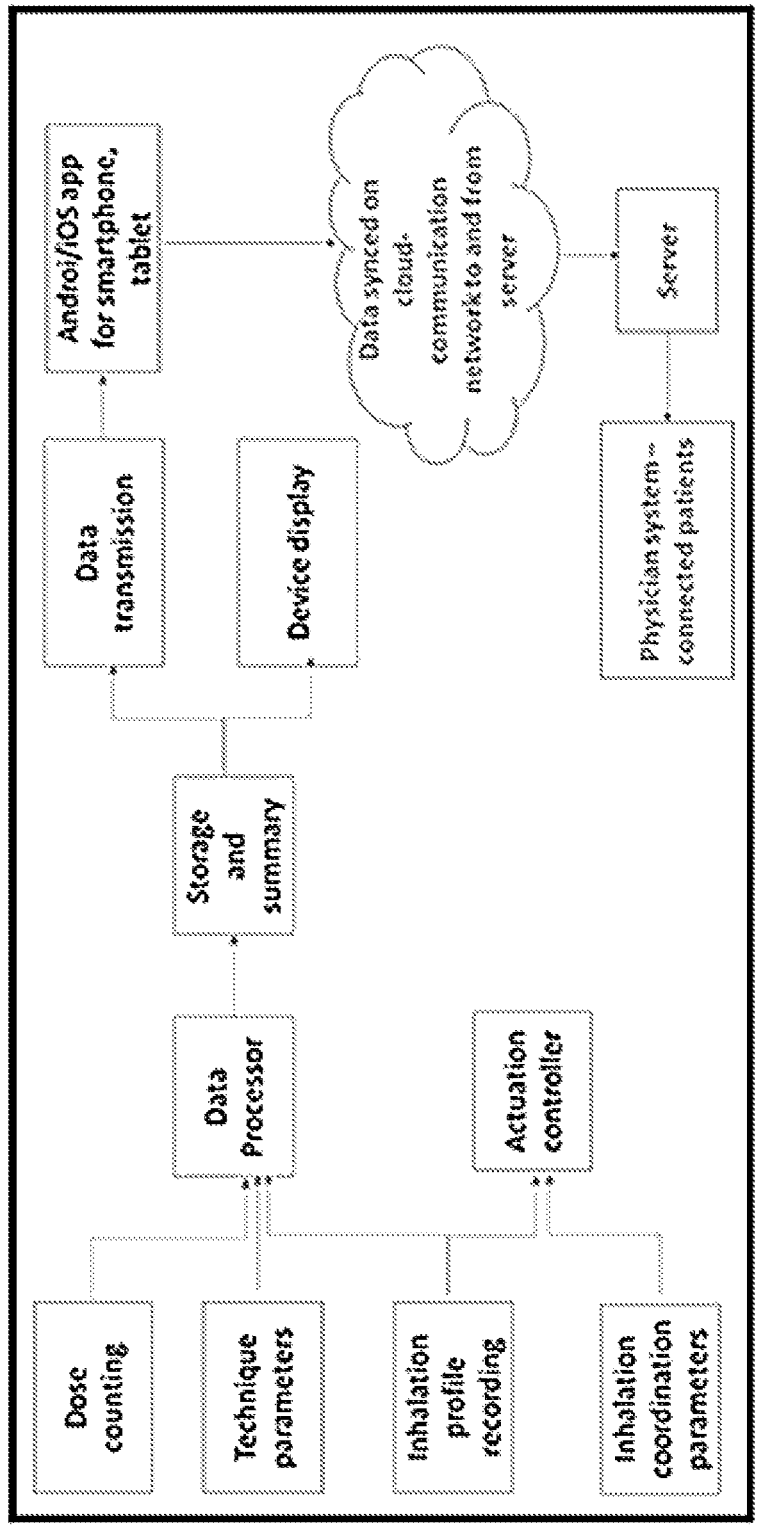
FIG. 7 illustrates a processing-operation and exemplary output-data as obtained by the operation of the device, in accordance with an embodiment of the present subject matter.

FIG. 7 illustrates a block-diagram of the processing operation and exemplary output-data as obtained by the device 100, 400 upon having captured data pertaining to the operation. As mentioned before, the adherence-monitoring and tracking-device 100, 400 as removably connected to the MDI comprises an embedded system to capture the user-performed operation over the inserted MDI, process said captured details through a microcontroller, and render audio-visual representation at a display device In an implementation, the microcontroller is adapted to process data received from one or more sensors (i.e. pressure-sensors) and components (e.g. canister) to provide information pertaining to at least one of:
  dose left in the device,
  a schedule of the next dose based on a pre-stored prescription; and
  adherence to the dosage regime as a percentage and absolute number based on an elapse of time as well as drug prescribed;
  a real-time tracking of the inhalation flow rate and techniques;
  deriving an inhalation-profile of the user;
  identifying a triggering flow-rate by self-calibrating the inhalation profile In an implementation, the microcontroller upon having received data from said one or more sensors located within the device is adapted to determine correctness or error of operation due to execution of one or more of:
  a) number of steps in the inhalation maneuver
  b) shaking of the MDI before use,
  c) opening of the actuator cap,
  d) exhalation before inhalation,
  e) inhalation for a certain duration before and after spray is actuated; and
  f) closure or restoration of the cap; and
  g) preparation for the second dose,
    wherein said error of operation is triggered upon having referred said created inhalation-profile.

In an implementation, the microcontroller upon having received data from said one or more sensors located within the device is adapted to ascertain correctness in the technique of coordination between the inhalation and actuation based on one or more of:
  a) orientation of the MDI;
  b) timing of the actuation;
  c) inhalation flow-rate profile received from the device.

In an implementation, the microcontroller based on aforesaid processing causes:
  generation of consolidated data at-least based on dose-schedule, adherence, pre-stored medical-prescriptions for a patient;
  synchronization of the generated data periodically with an external-storage (cloud-based storage).
  recording of parameters involved in an inhalation-maneuver's schedule of the next dose based on a pre-stored prescription; and
  depiction of adherence to the dosage-regime as a percentage and/or absolute number as a function of time and/or drug prescribed.

In an implementation, the microcontroller based on aforesaid processing causes a display of one or more of:
  doses taken by the user;
  number of doses left in the canister
  validity of steps within the pMDI inhalation maneuver;
  validity of coordination between actuation and inhalation maneuver;
  alerts in respect of errors made during the preparation, usage or post usage of the pMDI device The alerts may be segregated into a first set of alerts labelling the inhalation-maneuvers as valid or invalid during the usage of the MDI, a second type of alerts during the non-usage of the MDI device; and a third type of alerts in respect of fitness of the assembly of the MDI.

Based upon data as generated pertaining to inhalation technique of user, number of dosages undertaken, historical inhalations by the user (i.e. inhalation profile), and a coordination as exhibited between the actuation and inhalation, etc., the processor/microcontroller prepares a data summary or report for sending to the user by deploying low 'Bluetooth' energy based data transfer mechanism. Accordingly, the recorded data is transmitted with respect to each actuation of the MDI to the application operating upon the smartphone.

Figure 8:
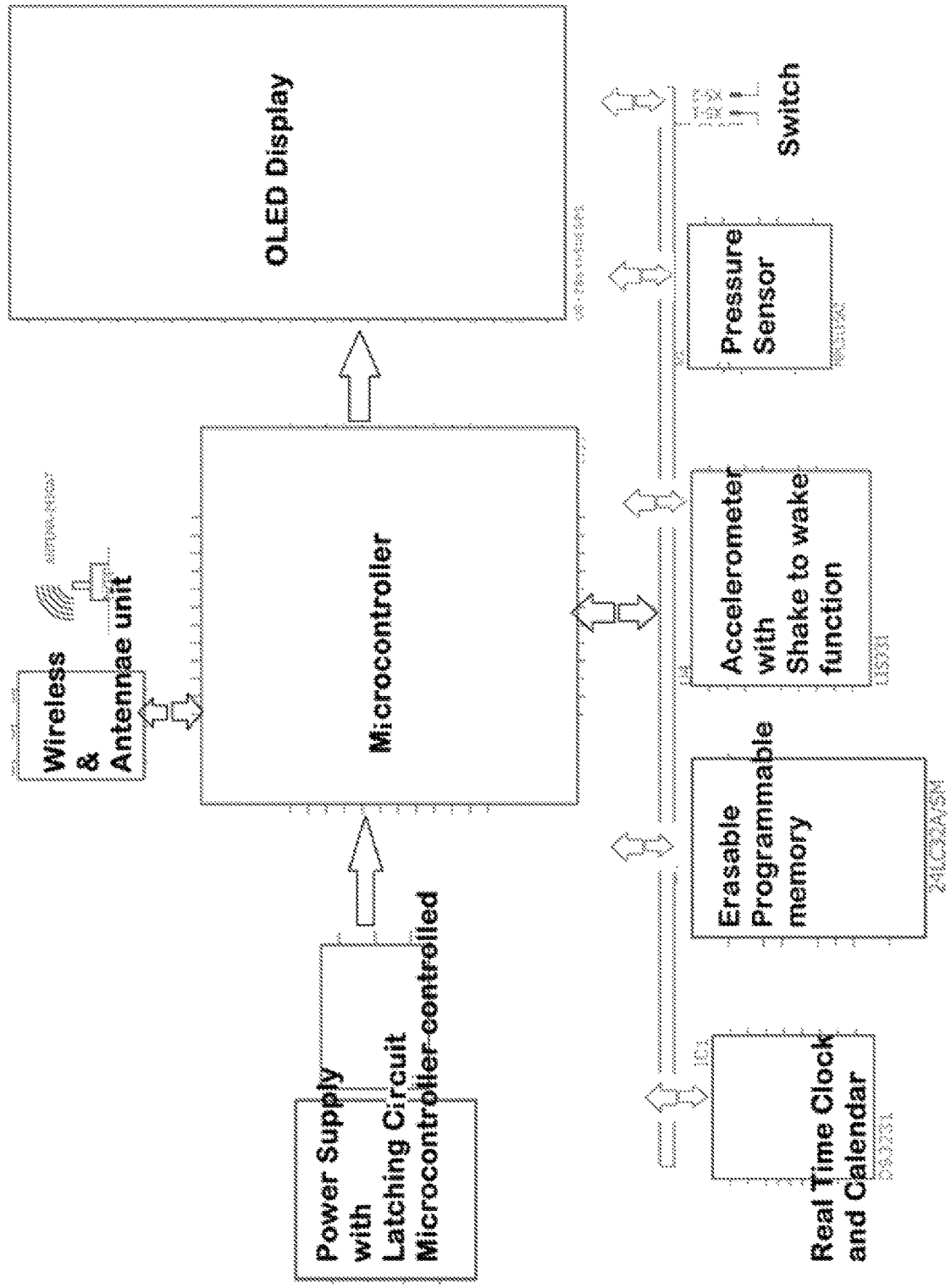
FIG. 8 illustrates a computing-architecture representation of the device, in accordance with an embodiment of the present subject matter.

FIG. 8 depicts a computing-architecture of the electromechanical system as the device 100, 400. More specifically, the present figure depicts a computing-system embedded within the jacket of the device 100, 400 and comprises:
  an assembly of power supply with a microcontroller enabled latch protection against over/under current,
  a microcontroller to perform the necessary decision-making functions as depicted,
  a real-time clock/calendar to maintain accurate time-keeping when main power to the device is interrupted,
  an EEPROM rendering a non-volatile memory source for storing data captured during the operation, an accelerometer for sensing a shake imposed upon the device and activating the jacket from sleep/stand-by state, a pressure-sensor (e.g. a piezoelectric sensor) for sensing the inhalation/exhalation pressure etc., an organic light-emitting diode (OLED) based display for rendering an output-display; and a wireless antennae for wirelessly and bi-directionally communicating with a remotely-located transceiver device, such as a mobile-phone.

Figure 9:
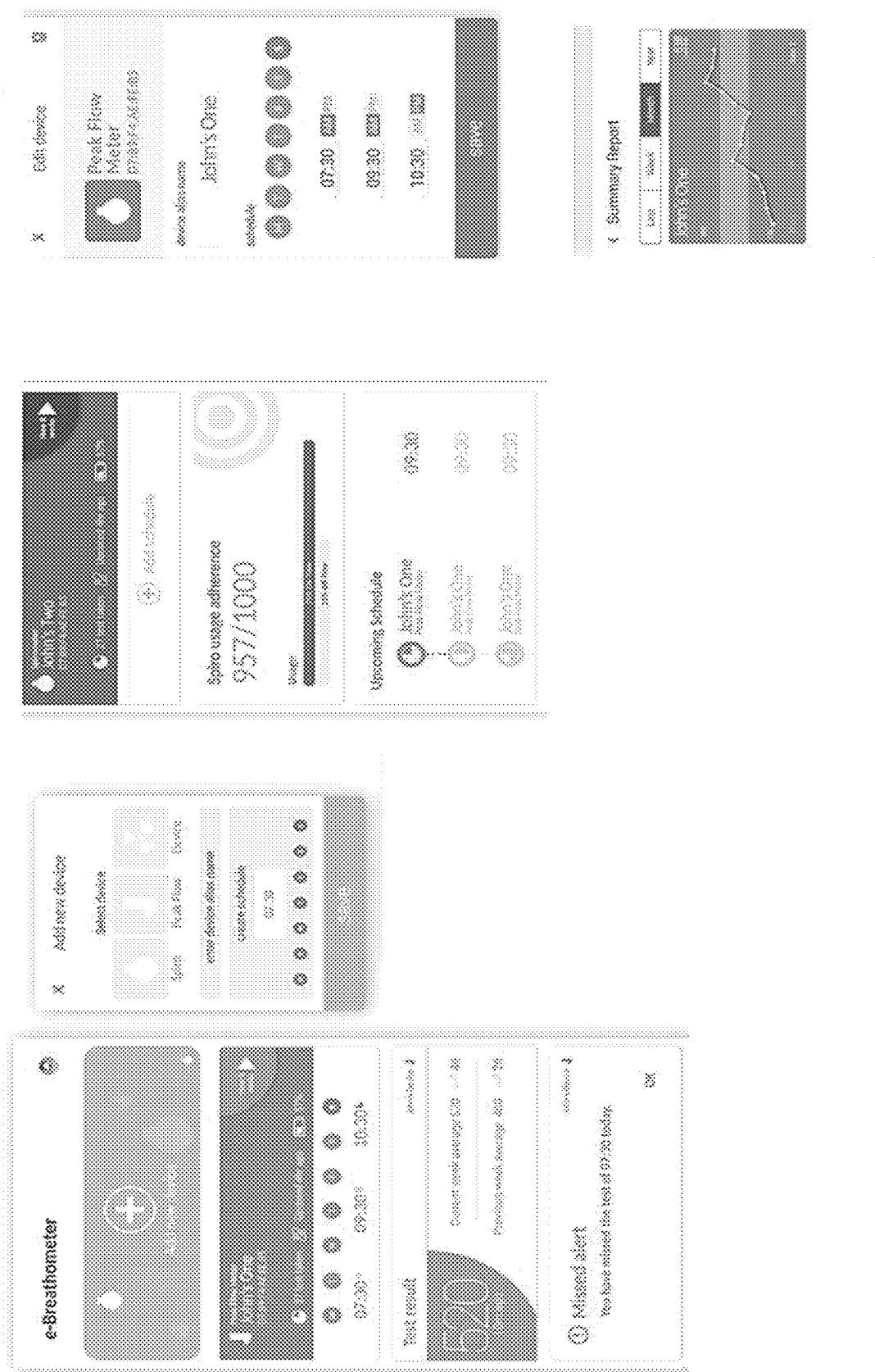
FIG. 9 illustrates schematic-views of the user-interface as rendered by an application linked with the device, in accordance with an embodiment of the present subject matter.

FIG. 9 depicts an exemplary user-interface of the application as implementable upon the smart-phone and linked to the device 100, 400, which receives the MDI within its enclosure. As may be evident, the user-interface's snapshots exemplarily illustrate patient-adherence with a usage of MDI, spirometer or peak-flow meter as received within the device 100, 400

The application linked with the device can be operated through a smartphone or tablet (e.g. Android and iOS platform). Said application as implemented within the smartphone uniquely identifies the patient, connects and pairs with it automatically, and receives the data transmitted by the device. More specifically, the application adapts to the user-behavior profile delivering specific number of messages, based upon consistency and adherence of the patient using the application. Moreover, the user can set his/her notification-preferences, such that notifications turn off if the patient has complied with his dose-regime. Moreover, the application is adapted to send notification in a push-notification form.

Overall, the device 100, 400 illustrated by the present subject matter offers a reusable electronic jacket in tandem with an application that can be hosted on mobile or tablet (both Android and iOS platform). The reusable electronic jacket provides a user with a programmable-electromechanical breath-actuated system that can be programmed to provide efficacious delivery of the selected medication to a given patient/user and keep track of the dose left in the canister of a given medication.

The electronic jacket is reusable and can be used with the conventional pMDI actuators without any need to modify the actuator or any flow constriction in the actuator flow path. It has a rechargeable battery which ensures that patient can reuse it for multiple actuators to track the adherence over a long period. The on-board microcontroller integrates the data from pressure sensors in the flow path to detect and map the inhalation profile of the patient, identify the triggering flow rate by self-calibrating the inhalation profile, and signal to the patient if the actuation of the drug was correctly coordinated with the inhalation flow rate.

The present device 100, 400 facilitates visual or audio-visual interaction with the patient, during and after actuation, using the display system or display cum sound-recorder system. This enables a system to give real-time notification of error in critical step during the inhalation-maneuver or the technique involved (e.g. patient forgets to shake before use, wrong actuation timing), and provide the summary of each of the above post usage using the display on the device.

An electronic chip controller attached with on-board device memory renders sufficient storage of complete data for the number of doses taken as well as details of each actuation, thereby eliminating the need for the device to be in proximity to the smart-phone when dose is taken. A further advantage is that with a tracking module having own internal memory, inhaler and smart phone can occasionally sync without possibility of losing data.

While specific language has been used to describe the disclosure, any limitations arising on account of the same are not intended. As would be apparent to a person in the art, various working modifications may be made to the method in order to implement the inventive concept as taught herein.

It is understood that the above description is intended to be illustrative, and not restrictive. It is intended to cover all alternatives, modifications and equivalents as may be included within the spirit and scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein.

Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. An adherence-monitoring and tracking device for capturing usage of a metered dose inhaler (MDI), the device comprising:

an enclosure configured to enclose the MDI; and an electro-mechanical system forming a part of the enclosure configured to sense and log an operation of the MDI, said electro-mechanical system comprising:

a microcontroller;

at least one transducer configured to capture one or more parameters pertaining to the operation of the MDI by a user, wherein the microcontroller is configured to process said captured one or more parameters at a periodic sampling interval of less than 10 milliseconds, wherein the microcontroller is configured to process the capture one or more parameters received from said at least one transducer during the operation of the MDI to ascertain:

a) a number of steps undertaken during an inhalation maneuver by the user;

b) shaking of the MDI before usage;

c) dislodgement of an actuator cap from the MDI;

d) occurrence of exhalation before inhalation;

e) inhalation for a certain duration before and after generation of spray; and f) restoration of the actuator at the MDI, wherein the microcontroller is further configured to process the captured one or more parameters received from said one or more transducers to derive an inhalation-profile of the user; and to identify a triggering flow-rate based on the inhalation-profile, and wherein the microcontroller is further configured to determine at least one error of the operation of the MDI due to execution of one or more parameters of parameters a) to f), and wherein the at least one error of the operation is triggered in response to referring said inhalation-profile; and an output-unit configured to render data pertaining to the operation of the MDI.

2. The device of claim 1 wherein the at least one transducer is at least one of:
a pressure sensor,
an acoustic-sensor; and
an accelerometer.

3. The device of claim 1, wherein the microcontroller is further configured to process the captured one or more parameters received from the at least one transducer to determine one or more of:
(a) a remaining dose within the MDI; and
(b) a real-time tracking of an inhalation flow rate.

4. The device of claim 1, wherein the microcontroller is further configured to provide a plurality of alerts to certify correctness of a user-operation of the MDI based on at least one of:
(i) the inhalation-profile of the user; and
(ii) the ascertained parameters a) to f).

5. The device of claim 1, wherein the microcontroller is configured to process the one or more parameters received from the at least one transducer during the operation of the MDI to determine one or more of:
a) orientation of the MDI;
b) timing of an actuation; and
c) an inhalation flow-rate profile captured during the operation of the device;
to thereby ascertain a correctness in coordination between the inhalation and actuation.

6. The device of claim 1, wherein the microcontroller is further configured to:
consolidate data pertaining to one or more of:
a) the dose-schedule,
b) a historical adherence of the user to the dose-schedule, and
c) a pre-stored medical-prescription for the user;
synchronize the consolidated data periodically with an external-storage;
capture data pertaining to an inhalation-maneuver as part of a forthcoming dose in the dose-schedule; and
depict adherence of the user to the dose-schedule as a percentage and/or absolute number as a function of time and/or a drug prescribed.

7. The device of claim 6, wherein the output-unit triggered by the microcontroller is configured to render one or more of:
a number of dosages undertaken by the user;
an indicator of valid-coordination between actuation and the inhalation-maneuver during the usage of the MDI;
a first set of alerts labelling the inhalation-maneuvers as valid or invalid during the usage of the MDI;
a third type of alerts during a non-usage of the MDI device; and
a fourth type of alerts in respect of fitness of an assembly of the MDI.

8. A method of capturing usage of a metered dose inhaler (MDI) with the adherence-monitoring and tracking device of claim 1, the method comprising:

providing the adherence-monitoring and tracking device of claim 1;
enclosing the MDI;
sensing and logging the operation of the MDI, by capturing the one or more parameters pertaining to the operation of the MDI by the user and processing said captured one or more parameters; and
rendering the data pertaining to the operation of the MDI.

9. An adherence-monitoring and tracking device for capturing usage of a metered dose inhaler (MDI), the device comprising:
an enclosure for accommodating the MDI, wherein the enclosure comprises:
a hollow cylindrical-portion configured to receive the MDI;
a foldable-flap integral to the cylindrical-portion from a first end configured to cover a top portion of the MDI; and
a plurality of magnetic-contacts configured to latch a second end of the flap to the cylindrical-portion; and
an electro-mechanical system forming a part of the enclosure, and configured to capture an operation of the MDI and electronically render data thereof, the electro-mechanical system comprising:
a microcontroller;
at least one transducer configured to capture one or more parameters pertaining to the operation of the MDI by a user, wherein the microcontroller is configured to process said captured one or more parameters at a periodic sampling interval of less than 10 milliseconds, wherein the microcontroller is configured to process the captured one or more parameters received from said at least one transducer during the operation of the MDI to ascertain:
a) a number of steps undertaken during an inhalation maneuver by the user;
b) shaking of the MDI before usage;
c) occurrence of exhalation before inhalation;
d) inhalation for a certain duration before and after generation of spray; and
e) restoration of an actuator of the MDI, wherein the microcontroller is further configured to process the captured one or more parameters received from said one or more transducers to derive an inhalation-profile of the user; and to identify a triggering flow-rate based on the inhalation-profile, and wherein the microcontroller is further configured to determine at least one error of the operation of the MDI due to execution of one or more parameters of parameters a) to f), and wherein the at least one error of the operation is triggered in response to referring said inhalation-profile.

10. A method of capturing usage of a metered dose inhaler (MDI) with the adherence-monitoring and tracking device of claim 9, comprising:
providing the adherence-monitoring and tracking device of claim 9;
accommodating the MDI within the hollow cylindrical-portion of the enclosure;
covering the top portion of the MDI with the foldable-flap flap;
latching the second end of the flap to the cylindrical-portion with the plurality of magnetic-contacts; and
capturing the operation of the MDI and electronically rendering the data thereof.

11. An adherence-monitoring and tracking device for capturing usage of a metered dose inhaler (MDI), the device comprising:
- a housing configured to accommodate the MDI defined by an assembly of a canister and a mouth-piece, wherein the housing comprises:
  - an elongated hollow-block open at a bottom of the housing configured to accommodate a canister of the MDI; and
  - a cover hinged at the bottom of the hollow-block, wherein said hinged cover is rotatable to act as a removable-lid at the bottom of the hollow-block and thereby selectively cover a mouthpiece linked to the canister accommodated in the hollow-block; and
  - an electro-mechanical system supported within the housing, and configured to capture an operation of the MDI and electronically-render data associated thereto, the electro-mechanical system comprising:
    - a microcontroller;
    - at least one transducer configured to capture one or more parameters pertaining to the operation of the MDI by the user, wherein the microcontroller is configured to process said captured one or more parameters at a periodic sampling interval of less than 10 milliseconds, wherein the microcontroller is configured to process the captured one or more parameters received from said at least one transducer during the operation of the MDI to ascertain:
      - a) a number of steps undertaken during an inhalation maneuver by the user;
      - b) shaking of the MDI before usage;
      - c) dislodgement of an actuator cap from the MDI;
      - d) occurrence of exhalation before inhalation;
      - e) inhalation for a certain duration before and after generation of spray; and
      - f) restoration of an actuator of the MDI, wherein the microcontroller is further configured to process the captured one or more parameters received from said one or more transducers to derive an inhalation-profile of the user; and to identify a triggering flow-rate based on the inhalation-profile, and wherein the microcontroller is further configured to determine at least one error of the operation of the MDI due to execution of one or more parameters of parameters a) to f), and wherein the at least one error of the operation is triggered in response to referring said inhalation-profile.

12. The device of claim 11, wherein a top of the hollow-block is configured to act as a guide for allowing the user to impose downward-push to the canister for operating the MDI.

13. The device of claim 11, wherein the hollow-back comprises at least one of:
- a set of internal ribs configured to rigidly accommodate the MDI; and
- a set of external ribs configured to allow a grip.

14. The device of claim 11, further comprising:
- a display connected to the electro-mechanical system and supported at an external surface of the hollow-block and configured to electronically render data and alerts; and
- one or more illuminators connected to the electro-mechanical system and supported at the external surface of the hollow-block to provide visible-alerts.

15. The device of claim 11, further comprising:
- a lock configured to latch the cover with the hollow-block to thereby cause a rigid-accommodation of the mouth-piece within the cover during non-usage of the MDI, wherein the lock comprises flexible flaps.

16. A method of capturing usage of a metered dose inhaler (MDI) with the adherence-monitoring and tracking device of claim 11, the method comprising:
- providing the adherence-monitoring and tracking device of claim 11;
- accommodating the MDI within the housing;
- accommodating the canister of the MDI in the elongated hollow-block;
- rotating the cover to act as the removable-lid at the bottom of the hollow-block and thereby selectively covering the mouth-piece linked to the canister accommodated in the hollow-block; and
- capturing the operation of the MDI and electronically rendering the data thereof.

* * * * *